US009962136B2

(12) United States Patent
Pratx

(10) Patent No.: US 9,962,136 B2
(45) Date of Patent: May 8, 2018

(54) RECONSTRUCTING TIME-VARYING POSITION OF INDIVIDUAL RADIOACTIVE CELLS DIRECTLY FROM POSITRON EMISSION TOMOGRAPHY (PET) MEASUREMENTS

(71) Applicant: The Board of Trustees of the Leland Stanford Junior University, Palo Alto, CA (US)

(72) Inventor: Guillem Pratx, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 335 days.

(21) Appl. No.: 14/711,396

(22) Filed: May 13, 2015

(65) Prior Publication Data
US 2015/0355347 A1 Dec. 10, 2015

Related U.S. Application Data

(60) Provisional application No. 62/007,651, filed on Jun. 4, 2014.

(51) Int. Cl.
*A61B 6/00* (2006.01)
*A61B 6/03* (2006.01)
(52) U.S. Cl.
CPC ............ *A61B 6/5264* (2013.01); *A61B 6/037* (2013.01); *A61B 6/486* (2013.01); *A61B 6/508* (2013.01)

(58) Field of Classification Search
None
See application file for complete search history.

(56) References Cited

U.S. PATENT DOCUMENTS

| 4,224,303 | A | * | 9/1980 | Shaw | ................. | A61K 51/1258 |
| | | | | | | 423/249 |
| 8,507,868 | B2 | | 8/2013 | Maucec | | |
| 2001/0031920 | A1 | * | 10/2001 | Kaufman | ............... | A61B 5/055 |
| | | | | | | 600/431 |
| 2007/0265528 | A1 | | 11/2007 | Xu et al. | | |

(Continued)

OTHER PUBLICATIONS

Brasse et al. 2005. Correction Methods for Random Coincidences in Fully 3D Whole-Body PET: Impact on Data and Image Quality. Journal of Nuclear Medicine. vol. 46, Issue No. 5, pp. 859 and 866.*

(Continued)

*Primary Examiner* — Jonathan Cwern
(74) *Attorney, Agent, or Firm* — Lumen Patent Firm

(57) ABSTRACT

A method of reconstructing time-varying position of individual radioactive point sources directly from Positron Emission Tomography (PET) measurements is provided that includes using a PET scanner to acquire list-mode coincidence events of a moving radioactive point source, using an appropriately programmed computer to model a trajectory of the moving radioactive point source as a 3D function of a temporal variable, then apply an optimization procedure to find the trajectory that minimizes a distance between the trajectory and the recorded list-mode coincidence events, and using the PET scanner to output a real time position of the radioactive point source.

5 Claims, 7 Drawing Sheets

(56) References Cited

U.S. PATENT DOCUMENTS

2008/0099685 A1* 5/2008 Karp ................. G01T 1/2985
 250/363.03
2010/0316275 A1* 12/2010 Stolin ................. G06T 11/006
 382/131

OTHER PUBLICATIONS

Magdics et al. Total Variation Regularization in PET Reconstruction. 2011. [Online]: http://www.cs.cornell.edu/~bkovacs/resources/99135.pdf. (p. 3).*
Parker et al. 1993. Positron emission particle tracking—a technique for studying flow within engineering equipment. Nuclear Instruments and Methods in Physics Research Section A: Accelerators, Spectrometers, Detectors and Associated Equipment. vol. 326, Issue 3, pp. 595 and 607.*

* cited by examiner

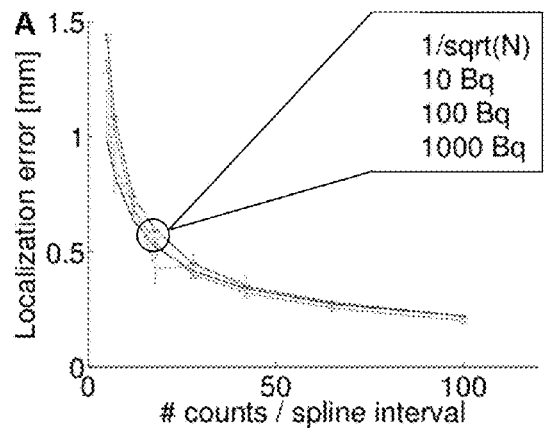
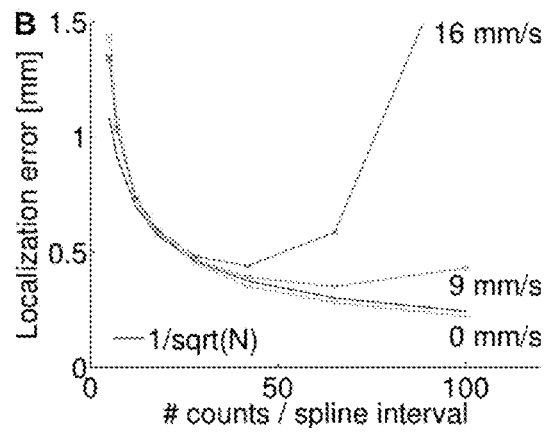
FIG. 7A   FIG. 7B
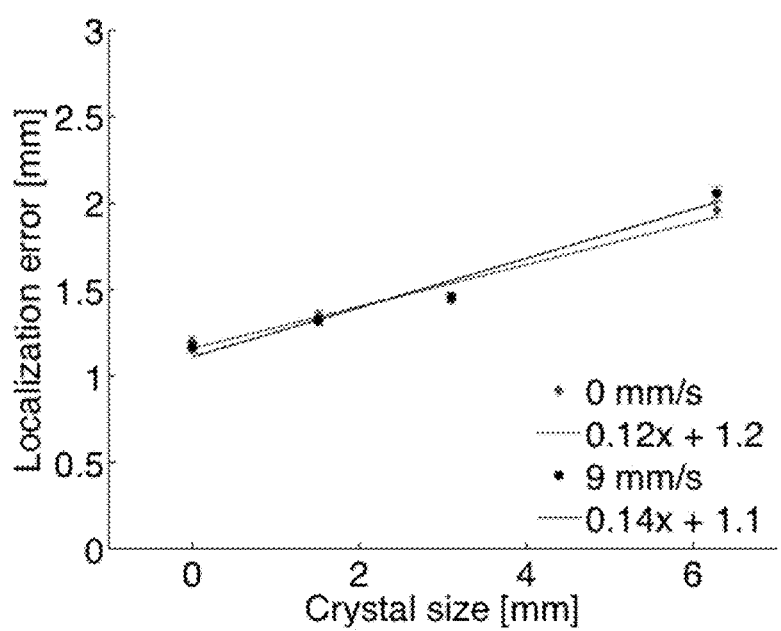
FIG. 8

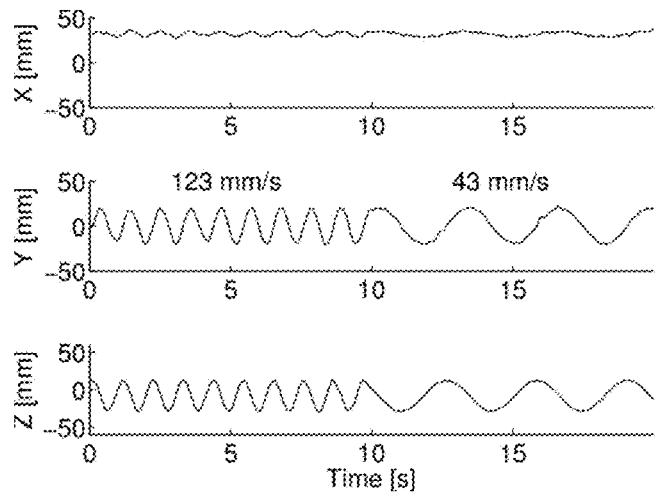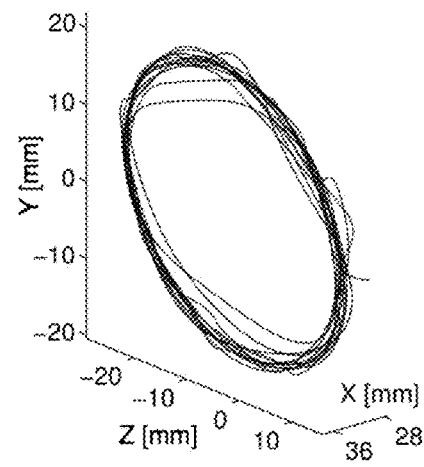
FIG. 9A
FIG. 9B
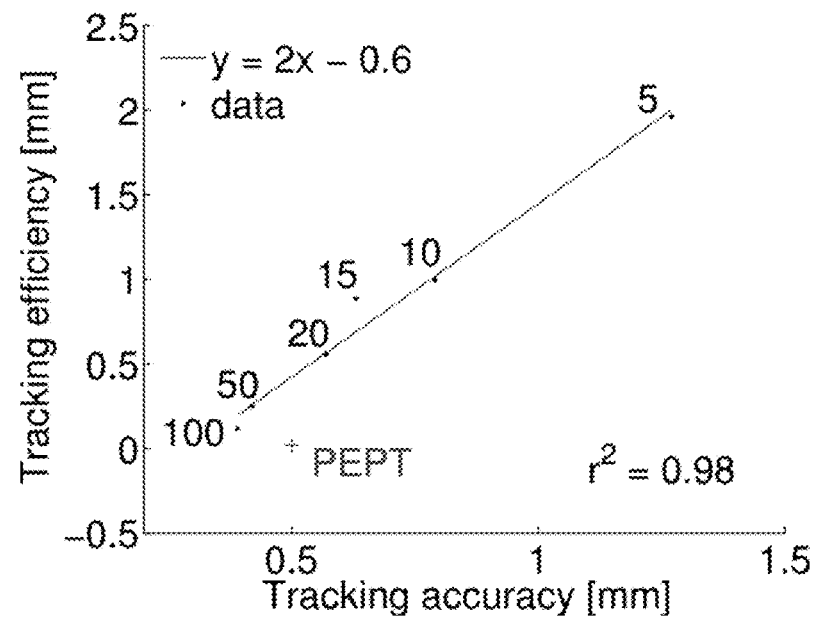
FIG. 10

RECONSTRUCTING TIME-VARYING POSITION OF INDIVIDUAL RADIOACTIVE CELLS DIRECTLY FROM POSITRON EMISSION TOMOGRAPHY (PET) MEASUREMENTS

CROSS-REFERENCE TO RELATED APPLICATIONS

This application claims priority from U.S. Provisional Patent Application 62/007,651 filed Jun. 4, 2014, which is incorporated herein by reference.

STATEMENT OF GOVERNMENT SPONSORED SUPPORT

This invention was made with Government support under contracts CA114747 and HL127900 awarded by the National Institutes of Health. The Government has certain rights in the invention.

FIELD OF THE INVENTION

The current invention relates to Positron Emission Tomography (PET). More specifically, the invention relates to a method of tracking the motion of one or more single cells in a living organism (e.g. mouse, patient), and tracking the motion of a radioactive target (e.g. tumor, etc.) in real time, using PET.

BACKGROUND OF THE INVENTION

Positron emission tomography (PET) is used for a variety of applications, ranging from clinical oncology and cardiology to pre-clinical drug discovery and neuroscience. Virtually all PET applications rely on the same workflow, which involves reconstructing one or more images representing the time-varying distribution of a radiotracer. These images can later be processed and analyzed to extract biologically relevant parameters such as standardized uptake value. Increasingly, however, PET is used in "tracking" applications, for which the "imaging" paradigm may not be optimal.

Cell tracking is a method that involves labeling cells ex vivo using a contrast agent and imaging their time-varying distribution in vivo. Clinically, the most common use of cell tracking is for tracking white blood cells to identify occult sites of infection or inflammation. More recently, advances in stem cell science and immunology have led to new cell-based therapies for cardiac, neural, and pancreatic tissue regeneration and cancer immunotherapy. Cell tracking is also widely used as a preclinical research tool to study biological processes such as cancer metastasis. Transplanted cells can be labeled and imaged non-invasively using magnetic resonance imaging (MRI), positron emission tomography (PET), single-photon emission computed tomography (SPECT), and optical imaging. So far, no consensus has been reached on which imaging modality is best suited for cell tracking MRI is the only imaging modality that has shown the capability to image single cells in vivo, but only for a few anatomical sites such as the brain and the liver; furthermore, MRI lacks sufficient temporal resolution to track single cells circulating in the bloodstream and homing to sites of infection or injury.

Of all the existing imaging modalities, PET has the highest molecular sensitivity and thus offers the most promising path towards tracking single cells in vivo and at the whole-body level. However, conventional algorithms used for reconstructing PET images are not optimal for tracking the trajectory of a single cell. The output of a conventional PET scan—large 3D images with millions of elements—is poorly suited for representing a single moving point source with high temporal resolution. This inefficient representation leads to an ill-posed reconstruction problem, meaning that millions of image elements must be computed from a small number of recorded PET coincidence measurements. Furthermore, a sequence of tomographic images is inefficient at representing the continuous motion of a sparse set of sources because it implies a discretization of space and time. As a result, PET images reconstructed from low-activity point sources are noisy and not suitable for tracking a moving source. A few strategies have been proposed to reconstruct dynamic PET images that are continuous along the temporal dimension, but these methods still represent the spatial dimension as a matrix of discrete elements. Alternatives to conventional image reconstruction for tracking single positron-emitting sources using PET have been proposed and investigated, especially in the field of chemical engineering. Early studies have shown that single particles labeled with a positron emitting radionuclide can be used as tracers to analyze complex patterns of fluid and powder flows in chemical processes. The technique was later refined and became known as positron emission particle tracking (PEPT). Unlike PET, PEPT uses a minimum-distance algorithm to localize a single moving source directly from PET measurements, that is, without reconstructing a tomographic image. Because the radiotracer is confined to a single particle, the reconstruction problem can be reformulated as a localization task and the position of the particle can be estimated directly from raw PET measurements, by finding the point in space that minimizes the average distance to the recorded coincidence lines. PEPT further uses an iterative algorithm to reject scattered and random coincidences. By splitting coincidence events into temporal frames, PEPT makes it possible to estimate the time-varying position and velocity of a single moving particle. PEPT has been applied to a variety of problems in the chemical engineering world, including mapping the dynamic behavior of opaque fluids, and the flow structure in fluidized beds and in canned foodstuffs. A variation of PEPT has also been developed to simultaneously track two independent particles.

In most PEPT studies, single particles are labeled with 1-30 MBq of $^{18}F$ and tracked using a dual-panel PET camera. However, it is likely impossible to label single cells with such high levels of activity. What is needed is a method of tracking single cells in vivo that can provide robust positioning using a reduced number of detected counts.

SUMMARY OF THE INVENTION

To address the needs in the art, a method of reconstructing time-varying position of individual radioactive point sources directly from Positron Emission Tomography (PET) measurements is provided that includes using a PET scanner to acquire list-mode coincidence events of a moving radioactive point source, using an appropriately programmed computer to model a trajectory of the moving radioactive point source as a 3D function of a temporal variable, then apply an optimization procedure to find the trajectory that minimizes a distance between the trajectory and the recorded list-mode coincidence events, and finally output a real-time position of the radioactive point source.

According to one aspect of the invention, the 3D function includes a B-spline function of the temporal variable. In one aspect here, a regularization term is added to the B-spline function to favor desirable trajectories over undesirable trajectories, where if no coincidence events are detected over a pre-defined time interval, a shortest trajectory is selected from available the coincidence events.

In a further aspect of the invention, the distance includes a mean-square distance between the trajectory and the recorded list-mode coincidence events.

In another aspect of the invention, the distance includes a likelihood function.

According to a further aspect of the invention, coincidence events that are further away than a predefined distance $d_{max}$ are assigned a value that is no greater than the $d_{max}$.

In yet another aspect of the invention, the PET scanner is built from non-lutetium scintillator materials comprising bismuth germinate (BGO) or lanthanum bromide (LaBr$_3$) to minimize background interference caused by intrinsic radioactivity.

According to another aspect of the invention, the output of the real time position of the radioactive point source includes an estimated tumor position in real time, estimated blood flow in real time, or estimated individual cell migration in real time.

BRIEF DESCRIPTION OF THE DRAWINGS

(FIG. 2B) the optimal trajectory (black curved line) is estimated by finding the 3D spline that has minimum mean-square distance to the recorded coincidence events (dashed lines); tracking is performed in 3D but, for simplicity, only two spatial dimensions are shown, according to one embodiment of the invention.

(FIG. 4B) Same data, processed using a single backprojection. (FIG. 4C) Source trajectory estimated directly from list-mode data using the minimum distance method used in PEPT, which splits the events into independent frames. (FIG. 4A) Same data, reconstructed using a third-order B-spline. Spline parameters were optimized for each activity level, according to the current invention.

(FIG. 6A) Localization error as a function of source velocity for a 10 and 100 Bq source. (FIG. 6b) Localization error as a function of source activity for a 9 and 100 mm/s velocity source. (FIG. 6c) Localization error as a function of source activity and velocity. The dashed line delineates the highest source velocity that can be tracked with <3 mm tracking error for a given activity. (5 counts/spline interval), according to the current invention.

FIGS. 7A-7B show influence of the number of spline knots on localization error. (FIG. 7A) Localization error as a function of the number of spline knots for a static source containing 10, 100, and 1000 Bq. (FIG. 7B) Localization error as a function of the number of spline knots for a 1000 Bq source moving with a velocity of 0, 9, and 16 mm/s. Error bars from 10 realizations, according to the current invention.

FIG. 8 shows localization error as a function of detector crystal size, shown for a 100 Bq source moving at 0 and 9 mm/s, respectively (R2=0.95; Error bars from 10 independent realizations; 5 counts/spline interval), according to the current invention.

FIGS. 9A-9B show experimental validation using a 1000 Bq-equivalent point source. (FIG. 9A) Estimated position of the source as a function of time. (FIG. 9B) 3D representation of the reconstructed trajectory. (10 counts/spline interval), according to the current invention.

FIG. 10 shows trade-off between tracking efficiency and accuracy, shown for a range of spline interval length, ranging from 5 counts/interval to 100 counts/interval, according to the current invention.

DETAILED DESCRIPTION

The current invention is a new method for tracking moving sources labeled with positron-emitting radionuclides using PET. In one aspect, provided is a new mathematical formalism that enables the time varying position of these sources to be estimated from a very small number of coincidence measurements. Thus, low-activity and fast-moving sources can reliably tracked in vivo with <2 mm accuracy. This method can be applied for real-time tracking of a moving tumor, estimation of respiratory breathing in 4D-PET, or tracking of single cells in vivo.

The current invention provides a method to localize the time-varying position of individual sources directly from raw list-mode PET, thereby bypassing conventional image reconstruction entirely.

The invention is a new "trajectory reconstruction" algorithm that can estimate the trajectory of a moving source directly from list-mode data. According to one embodiment, a source is a single object that is labeled with a certain amount (e.g. 1-1000 Bq) of a positron-emitting radionuclide (e.g. 18F, 11C, 64Cu, 89Zr, etc.). The trajectory is represented by a 3D spline function of the temporal variable. An objective function is derived that represents the average distance between the spline trajectory and a list of coincidence lines (i.e. list-mode dataset). An optimization procedure is used to find the trajectory that minimizes the objective function. This trajectory is the optimal estimate of the time-varying motion of the positron source.

Although the current invention relates to tracking a single moving source, it is possible to extend this formalism to the tracking of multiple moving sources in parallel.

The invention is the first method provided to reconstruct the motion of a source directly from PET measurements, without forming an image.

The current invention provides a tracking scheme in conjunction with biomedical imaging for tracking a single cell moving within a body. To address the issue of low radioactivity, an improved localization scheme is provided that uses a spline function to represent the time-varying position of a cell as a function of time. This method is advantageous because it represents space and time as two continuous quantities, and it represents the trajectory of a cell as a smooth function. Other types of smooth functions may also be used to represent the trajectory of the source, as it is known in the art.

Figure 1:
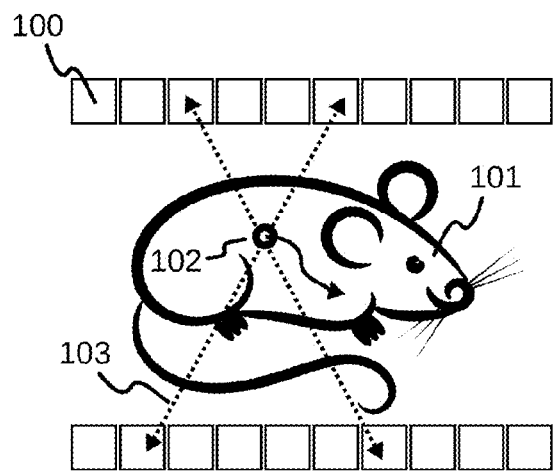
FIG. 1 shows an overview of the acquisition set-up, where a PET system (100) is used to localize a moving source (102) within a living system (101), and the source, which is labeled with a suitable positron emitting radionuclide, emits coincident pairs of annihilation photons (103), which can be detected by the PET system, wherein these events can be processed to yield a real-time position of the source, according to one embodiment of the invention.

FIG. 1 shows an overview of the acquisition set-up, where a PET system (100) is used to localize a moving source (102) within a living system (101), and the source, which is labeled with a suitable positron emitting radionuclide, emits coincident pairs of annihilation photons (103), which can be detected by the PET system, wherein these events can be processed to yield a real-time position of the source, according to one embodiment of the invention.

Figure 2A:
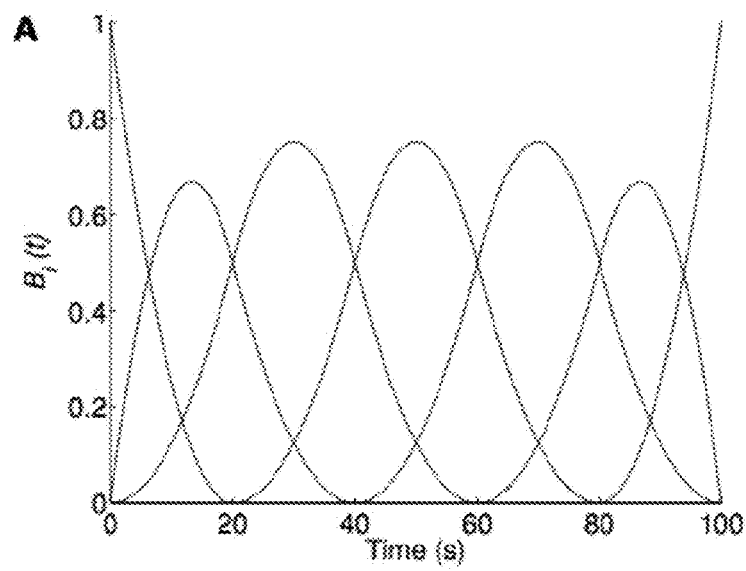
FIGS. 2A-2B show the trajectory reconstruction algorithm, (FIG. 2A) example of cubic B-spline basis functions used to model the time-varying trajectory of a single moving source (N=7 basis functions)

Provided is a new method for tracking the position of a single moving point source directly from raw PET data, where the trajectory of the moving source is represented as a 3D B-spline function of the temporal variable. A spline is a piecewise polynomial, where the intervals are delineated by spline "knots". The spline function and its derivatives remain continuous at the spline knots. Splines can be represented in several ways. The current invention uses the B-spline representation, which decomposes the spline as a weighted sum of basis functions (FIG. 2A). Thus, the trajectory of a moving point source can be represented as $$r(t) = \sum_{i=1}^{N} a_i B_i(t), \quad (1)$$

where $B_i(t)$ are 1D spline basis functions, $a_i = (a_i^x, a_i^y, a_i^z)$ are spline coefficients and N is the number of basis functions used in the model. This model naturally incorporates the knowledge that the trajectory is a smooth and continuous function, and requires no discretization of the spatial or temporal variable. Furthermore, a complete trajectory can be described using only 3N variables, far fewer than the size of a 4D PET image. The parameter N, which controls the number of basis functions, allows the model to be adjusted as needed.

Turning now to the objective function, PET forms images by acquiring coinciding pairs of annihilation photons, which are emitted in opposing directions. When two events are detected nearly simultaneously, one can infer that a radioactive decay event occurred somewhere along the line than joins the two detectors. It is noted that, in principle, only two intersecting lines are required to localize a single static source in 3D.

Intuitively, this concept can be transposed to a moving source by using the continuous stream of lines provided by a list-mode PET acquisition. Each element of a list-mode dataset contains the time and coordinates of each coincidence event. This format is thus ideal for locating a moving source because it preserves the full spatial and temporal resolution of the measurements. The advantages of reconstructing tomographic images directly from list-mode data have long been recognized.

Figure 2B:
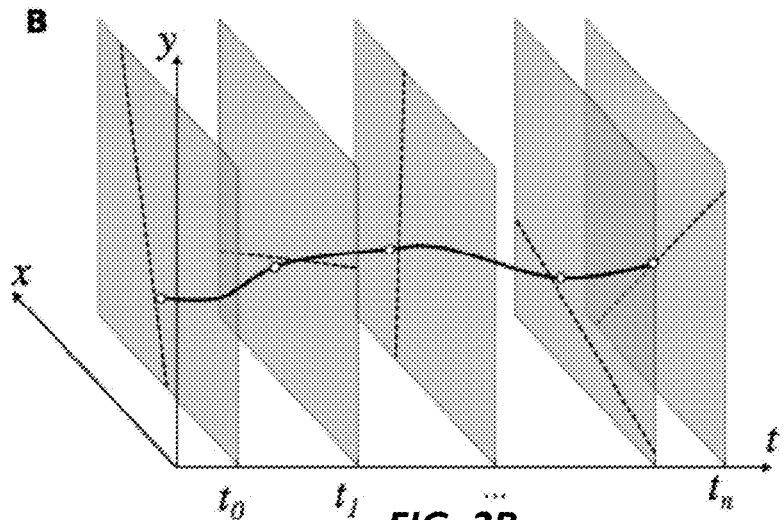

According to one embodiment, the current invention provides an algorithm for estimating the spatiotemporal trajectory r(t) of a moving point source given a set of list-mode coincidence events. In an ideal PET system with perfect spatial, temporal and spectral resolution, the trajectory of the moving source and the coincidence lines would intersect. Therefore, the current invention, which is illustrated in FIG. 2B, selects the source trajectory that minimizes the mean-square distance between the time-varying source position and the measured coincidence lines. By representing the trajectory as a spline function, the search space is limited to a small subset of smooth and continuous trajectories, the size of which is determined by the number of intervals N used to define the spline trajectory.

A list-mode data file contains spatial and temporal information for all recorded coincidence events. Here, we mathematically represent this information as follows. The line of response corresponding to event j shall be defined as the position of one of the detectors, which will be noted as $P_j$, and the unit-length direction of the line, which will be noted as $v_j$. The timestamp of the event will be noted as $\tau_j$. The Euclidian distance $d_j$ between line j and the corresponding point $M_j = r(\tau_j)$ that lies on the spline trajectory is then calculated using the following relationship:

$$d_j^2 = \|(\overrightarrow{M_j P_j})\|^2 - (\overrightarrow{M_j P_j} \cdot v_j)^2. \quad (2)$$

The mean-square distance between a given source trajectory r(t) and a set of K coincidence lines is given by $$I(a) = \frac{1}{K} \sum_{j=1}^{K} d_j^2. \quad (3)$$

This objective function is a quadratic function of the spline coefficients and can be minimized using standard convex optimization methods to yield the optimal estimate of the source trajectory.

With respect to the uniqueness of solution and regularization, for low-activity sources, it should be noted that the trajectory that minimizes I(a) may not be unique. As shown in FIG. 2A, the $i^{th}$ spline basis function is non-zero only within the interval $[t_{i-2}, t_{i+1}]$, thus if no count is recorded within that interval, $a_i$ is entirely decoupled from the objective function I(a). In that situation, it is impossible to objectively determine the value of $a_i$ and the algorithm may grossly misestimate the source trajectory. To circumvent this problem, we add a regularization (i.e. penalty) term R(a) to the objective function. This term, which is defined as $$R(a) = \frac{1}{N} \sum_{i=1}^{N-1} \|a_{i+1} - a_i\|^2 \quad (4)$$

favors trajectory for which the spline coefficients vary the least in the $L_2$ sense. In other words, if no coincidence events are detected over a prolonged time interval, the reconstruction algorithm extrapolates from surrounding events, implicitly favoring shorter trajectories (less variation in the position of the source) over longer ones. The strength of the regularization is adjustable using a parameter λ and was set to 0.005 in the experiments.

A variation solution is to space the spline knots non-uniformly such that coincidence events are equally distributed among spline intervals, thus ensuring that there are always enough counts within each spline interval.

In addition to the aforementioned effects, PET measurements are invariably corrupted by erroneous events that are indistinguishable from true coincidence events. These events are caused by accidental coincidences, scattered photons, and yield lines that do not pass near the true position of the source. Due to the strong quadratic penalty, these distant events would distort the reconstructed trajectory. To remediate this problem, $d_j$ is kept constant beyond a distance $d_{max}$. This strategy aims at reducing the impact of distant outliers, here scattered and random counts, and is thus an example of robust statistical estimation.

Using this principle, the objective function can be rewritten as $$J(a) = \frac{1}{K}\sum_{j=1}^{K} \min(d_j^2, d_{max}^2) + \lambda \cdot R(a). \quad (5)$$

This new objective is a non-convex function of the spline coefficients. Therefore, a conventional optimization method may converge to a different local minimum depending on the initial conditions. According to the current invention, the trajectory that minimizes I(a) is used as the starting point for minimizing J(a). While not guaranteed to converge to the global minimum, it was found that, in practice, this method yields satisfactory trajectories for a wide range of physical conditions. In the exemplary experiments described below, the parameter $d_{max}$ was set to 3 mm, which is approximately twice the crystal size for the Inveon, but any value between 2 and 6 mm resulted in suitable performance.

Figure 3:
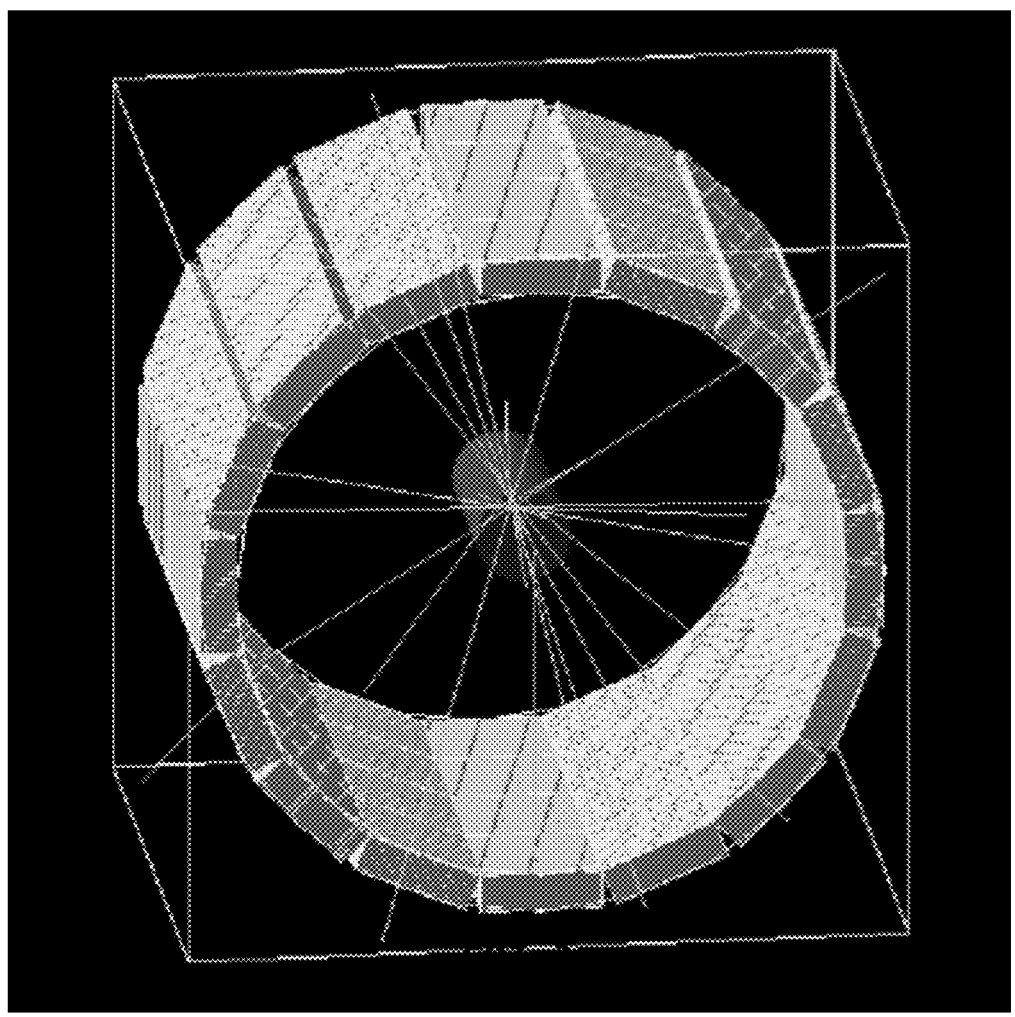
FIG. 3 shows a geometric model of the Inveon microPET, where the acquisition of listmode data was simulated using the GATE Monte Carlo package, according to one embodiment of the invention.
Figures 4A, 4B, 4C, 4D:
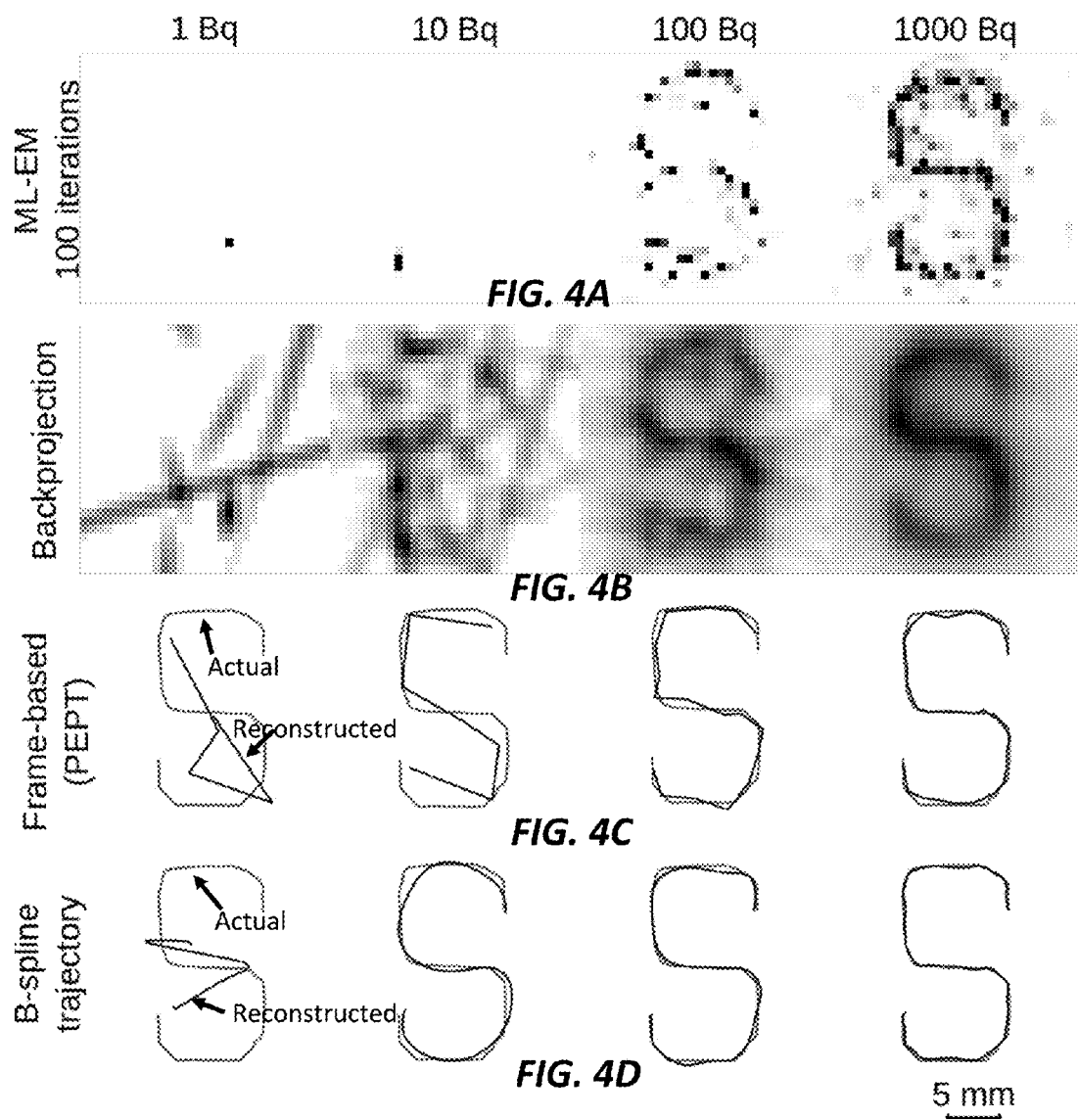
FIGS. 4A-4D shows (FIG. 4A) MLEM reconstruction of list-mode PET data from a point source (1, 10, 100, 1000 Bq) moving at 0.5 mm/s in an S pattern (100 iterations).

To validate the trajectory reconstruction algorithm, we used the GATE Monte Carlo package to simulate the acquisition of list-mode data from the Siemens Inveon microPET scanner (FIG. 3). The system geometry was implemented as previously described, using LSO as the detector material. The energy and time windows were set to 250-750 keV and 3.4 ns, respectively. Single events were positioned at the center of the crystal, at a depth of 3 mm. The simulation time was set to 100 s and divided into 10,000 time slices, thus providing a simulated temporal resolution of 10 ms. A single 18F point source was placed in a static water phantom which approximated the body of a mouse (a cylinder with a diameter of 2.5 cm and a height of 5 cm) and moved according to various predefined motion patterns, which are detailed in the Results section. Coincidence events generated by GATE were processed using Root and converted into a listmode data file. With these simulation settings, a sensitivity of 8.4% was achieved for a 1000 Bq static point source placed at the center of the system.

Unconstrained non-linear optimization of the objective function was implemented in MATLAB using the fminunc function, which is an implementation of the quasi-Newton line search method. This optimization method was chosen for its availability, although it is relatively slow. The maximum number of iterations was set to 2000, and the minimum step length to 0.01 mm.

The spatiotemporal trajectory of the source was represented using a 3D B-spline function of order 3. The number of spline intervals was chosen so that each interval contained an average of 5 counts. Spline knots were uniformly spaced and had single multiplicity except for the two knots at the extremities of the trajectory, which had triple multiplicity to allow for a discontinuity.

As a reference, PET images were reconstructed from simulated point sources (1, 10, 100, 1000 Bq) using standard maximum-likelihood expectation-maximization (MLEM), a popular reconstruction algorithm. Tomographic images (pixel size: 0.78125 mm×0.78125 mm×0.786 mm) were reconstructed directly from raw list-mode data using a previously developed GPU-accelerated package. Due to the low count statistics, ordered subsets were not used. The reconstruction procedure was carried out for 100 iterations, which was deemed sufficient for convergence purposes.

Also implemented was the "minimum-distance" method that is currently used in PEPT for tracking moving particles in fluid and powder systems. This method models the trajectory as a sequence of discrete frames, which are reconstructed independently. For each frame, the method aims to find the point in space that minimizes the average perpendicular distance to the coincidence lines within that frame. Thus, the minimum-distance method can be formulated as a special case of spline trajectory reconstruction, but with piecewise-constant basis functions (i.e. first-order B-spline). Thus, after optimization, the coefficients of the first-order B-spline correspond to the point in space that is closest to the lines recorded within the corresponding frames. The minimum-distance method was thus implemented by decreasing the order of the spline trajectory from 3 to 1. For comparison with third-order B-splines, the number of knots was kept the same and scatter and randoms rejection was implemented in the same manner.

The performance of the trajectory reconstruction algorithm was evaluated by computing the tracking accuracy, which we define as $$D^2 = \frac{1}{Q}\sum_{k=1}^{Q} \|r(\theta_k) - p_k\|^2, \quad (6)$$

where $\theta_k$ is a uniform subdivision of the time domain, Q=5000, and $p_k$ is the known simulated trajectory.

As a final validation, list-mode data of a moving $^{22}$Na point source (130 kBq) was acquired using an Inveon PET scanner (energy window of 350-650 keV, timing window of 3.4 ns). The point source was mounted onto a turntable powered by a stepper motor and scanned for 3 min. The rotation speed was initially set to 123±2 mm/s and was decreased halfway through the acquisition to 43±1 mm/s. List-mode data were retrieved from the Inveon workstation and imported into MATLAB for reconstruction. The reconstruction parameters were kept the same as in the Monte Carlo simulation study (5 counts/spline interval, $d_{max}$=3 mm, and $\lambda$=0.005). To simulate an even lower activity source, 97.8% of the acquired counts were randomly discarded, thus achieving count statistics equivalent to the previously simulated 1000 Bq source.

Turning now to a comparison with ML-EM and frame-based reconstruction, proposed trajectory reconstruction algorithm of the current invention was compared against standard list-mode MLEM (FIGS. 4A-4D). A point source (1, 10, 100, and 1000 Bq) following an S-like trajectory (0.5 mm/s) was simulated in GATE. List-mode data were generated and reconstructed using both MLEM and the novel trajectory reconstruction algorithm. For the 1000 Bq source, the pattern of the S trajectory was clearly visible in the MLEM image. However, with decreasing amounts of radioactivity, the MLEM images became noisier and no longer represented the accurate spatiotemporal trajectory of the moving point source, especially for physiologically achievable cell activities (i.e. less than 10 Bq). The first iteration of the reconstruction is a back projection of all the recorded counts and provides a lower noise image.

In contrast to tomographic image reconstruction, direct reconstruction of the source position from raw list-mode data was possible for activities as low as 10 Bq. Furthermore, with increasing amounts of radioactivity, tracking accuracy improved dramatically. It is noted that all methods failed to suitably track the 1 Bq source because of unsufficient count statistics.

A visual comparison of the trajectories reconstructed using the frame-based method used in PEPT and the spline-based method introduced in this article shows that the spline-based method can more accurately estimate the trajectory of the moving source. This is likely due to the fact that the framebased method does not account for the motion of the source within each temporal frame.

To better understand the capabilities and limitations of single-cell tracking with PET, a variety of point-source trajectories were simulated. Anticipating that the ability to track a moving point source would be determined both by the activity and velocity of the source, a single source (activity ranging from 1 to 1000 Bq) moving in a helical fashion (velocity ranging from 0.4 to 185 mm/s) inside a static water phantom was simulated. The range of velocities chosen in this experiment was meant to mimic the average blood flow velocity in humans, which ranges from 0.7 mm/s in capillaries to 400 mm/s in the aorta. Each Monte Carlo simulation was repeated 10 times (with different random seeds) to assess statistical significance.

Figure 5:
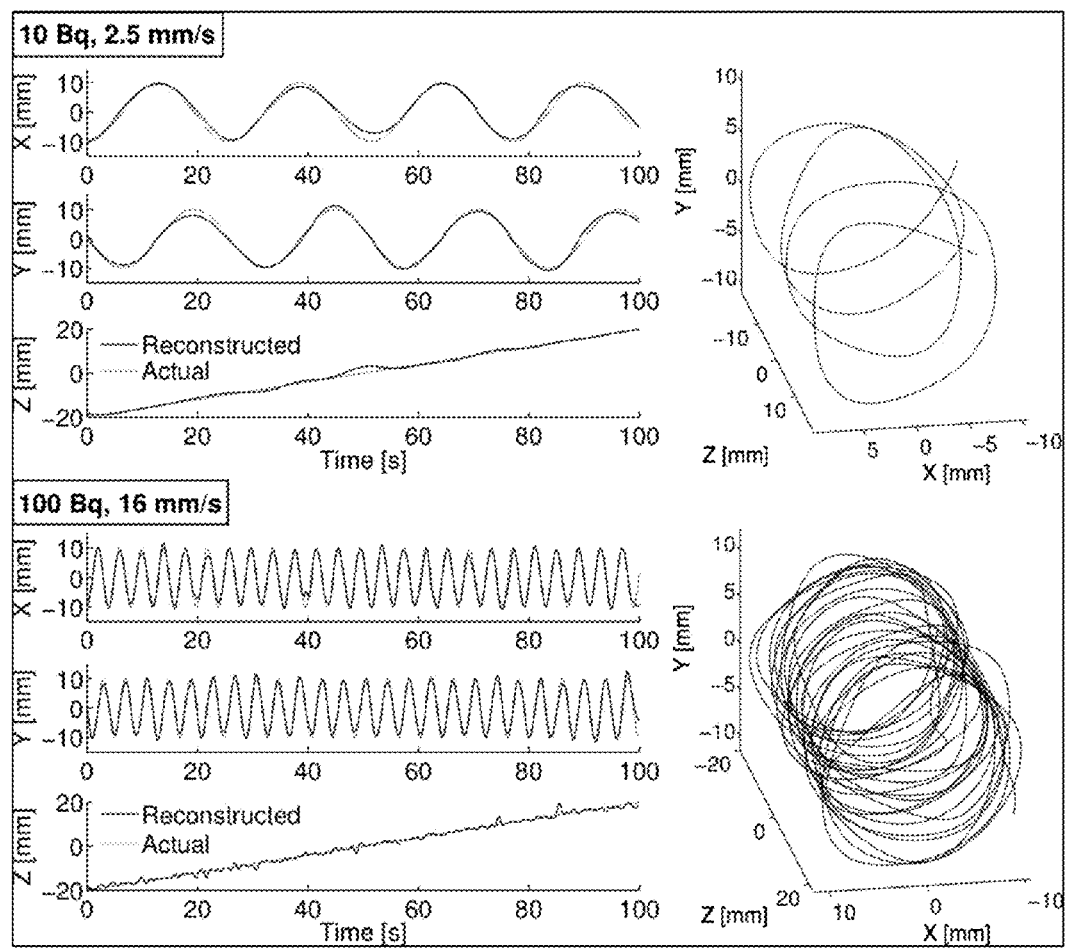
FIG. 5 shows two examples of source tracking: Left column: The reconstructed position of two moving sources (10 and 100 Bq) is compared against the known simulated trajectory (helical motion, 2.5 or 16 mm/s). Right column: 3D rendering of the reconstructed trajectory. (5 counts/spline interval), according to the current invention.

The simulations show that the spline reconstruction algorithm can track a single source over a wide range of velocities and activities. For instance, both a 10 Bq source moving 2.5 mm/s and a 100 Bq source moving 16 mm/s were tracked with average localization error better than 3 mm (FIG. 5). Videos of these trajectories are included online as supplemental information. The general pattern observed was that source tracking could lead to three possible outcomes, namely success, failure, or an intermediate state. For sufficiently low velocity (FIG. 6A) or sufficiently high activity (FIG. 6B), tracking was successful and achieved a constant localization error of ≈1.3 mm, independent of activity and velocity. In contrast, for certain combinations of low activities and high velocities, tracking simply failed, leading to poor tracking accuracy (i.e. >10 mm). Last, an intermediate outcome for which tracking was partially successful was observed, meaning that the shape of the reconstructed trajectory could be recognized but it significantly deviated from the reference trajectory. Additionally, for low activity sources, it was noticed that individual simulations of the same experiment showed a greater level of variability, compared to higher levels of activity.

Figure 6A:
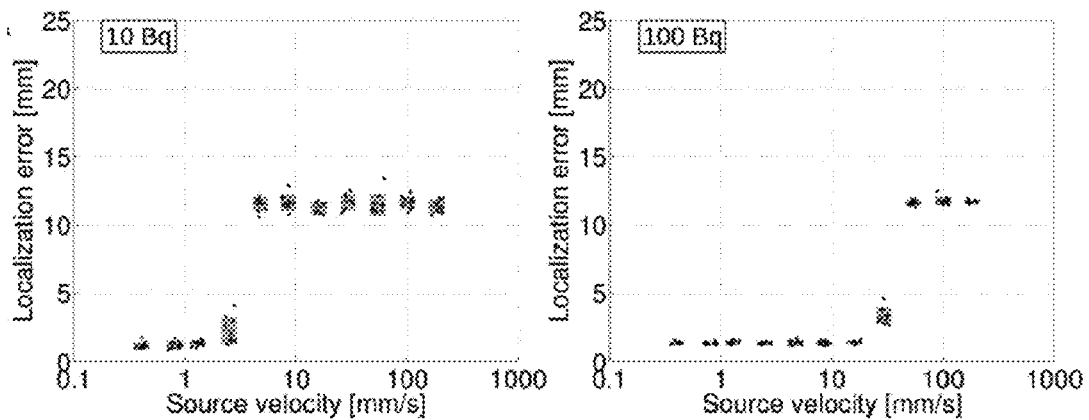
FIGS. 6A-6C show influence of activity and velocity on the localization of a single moving source.
Figure 6B:
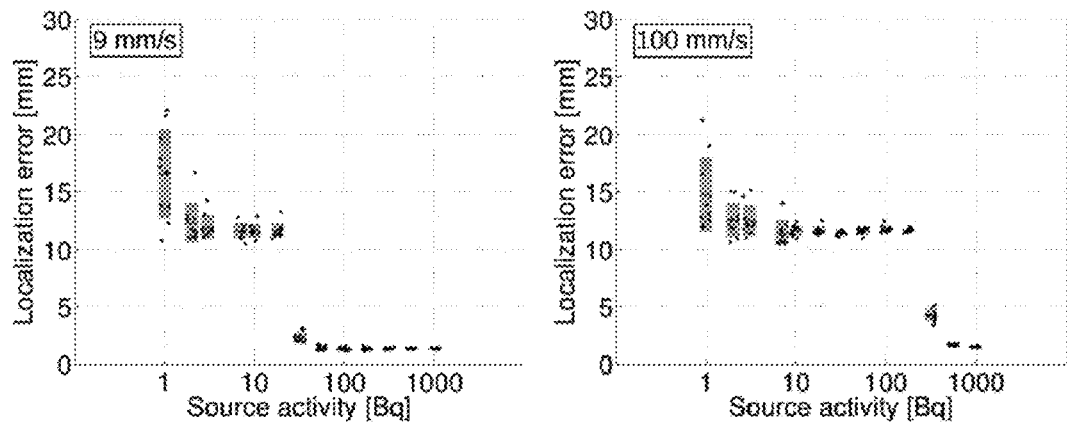
Figure 6C:
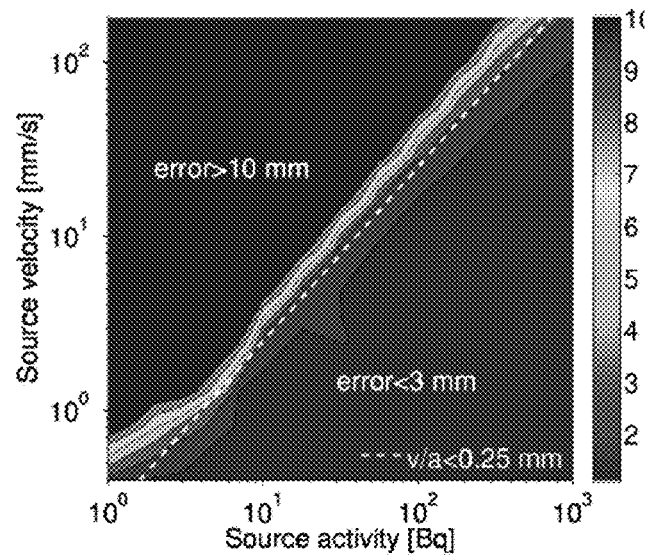

It was then sought to establish an empirical rule governing the feasibility of single-cell tracking, especially with regards to source velocity and activity. A source to be successfully tracked if tracking accuracy is better than 3 mm, was considered. Based on this criteria, a source can be tracked if its activity [Bq] is greater than four times its velocity [mm/s] (FIG. 6C, dashed line). For example, a single cell moving 2.5 mm/s must be labeled with at least 10 Bq (4×2.5) of activity to be successfully tracked (e.g. FIG. 5). This trend was observed over a wide range of velocities and activities.

Further investigated was how the number of intervals used in the B-spline model influenced the quality of the reconstructed trajectory. The same simulated helical motion was used to compare localization error when the number of spline intervals was varied. In general, tracking accuracy depends both on the absolute number of recorded counts and on the absolute number of spline intervals used in the reconstruction. However, a more thorough investigation revealed that tracking accuracy is really only a function of the ratio of these two quantities. In other words, as long as each spline interval contains, on average, a fixed number of counts, tracking accuracy is independent of source activity and velocity. FIGS. 6A-6B illustrate this point very clearly and show that the same tracking accuracy (1.3 mm) is achieved irrespective of source activity and velocity.

Now that it has been established that tracking accuracy only depends on one parameter, that is the number of counts per spline intervals, it was investigated how tracking accuracy is related to this parameter. First, the number of spline intervals used in the spline model was varied, thus varying the number of counts per spline interval from 5 to 100. It was observed that as more counts are available within each spline interval, the tracking accuracy of a static point source improves (FIG. 7A).

This result is expected since more independent measurements are combined to estimate the individual spline coefficients. It was also observed that the tracking accuracy is approximately proportional to $1/\sqrt{N}$, which is consistent with the averaging of N independent and identically distributed measurements.

For a moving point source (1000 Bq; 9 and 16 mm/s), it was observed that a similar pattern holds (FIG. 7B). With larger spline intervals, more counts are available for estimating individual spline coefficients and, therefore, the tracking accuracy improves. However, if the spline intervals are too large, the spline is too rigid and cannot represent the complex motion of the source. This highlights the need for tailoring the spline model to each application.

To evaluate the performance of the trajectory reconstruction algorithm, hypothetical variations of the Inveon scanner that were equipped with detector crystals of various sizes were simulated, including the standard size (1.59 mm), as well as larger crystals (3.10 and 6.28 mm, respectively). Also simulated was a perfect detector resolution (positron range and acolinearity effects were still included).

Reconstructed list-mode data was acquired from a 100 Bq point source, which was either static or moved at 9 mm/s. Unsurprisingly, these studies showed that larger crystals lead to less accurate tracking of the point source (FIG. 8). However, it was also found that the loss of tracking accuracy was quite moderate compared to the change in crystal size. Linear regression analysis show than a 1 mm increase in crystal size results in a modest 0.1 mm increase in localization error, independently of velocity.

The spline reconstruction method was experimentally validated by reconstructing list-mode data from a moving point source scanned on an Inveon PET/CT scanner. The circular trajectory of the source can be easily recognized (FIGS. 9A-9B). Notice that the rotation axis was not perfectly vertical, therefore some motion is seen along the X axis. Using Fourier analysis, the rotation frequency was measured and it was found to be 0.94 and 0.31 Hz, respectively, which matches the true rotation speed (0.95 and 0.33 Hz). The average rotation radius was measured (20.1 mm) and found to be consistent with the true radius (20.8 mm). Overall, these results confirm the validity of our computer simulations.

According to the current invention, in the exemplary experiment, it was found that PET can be used to track and reconstruct the trajectory of a single moving cell at the whole-body level, in a mouse. Such trajectory reconstruction methods have thus far only been used for 3D particle velocimetry in chemical engineering. Due to the unique constraints of live-cell tracking, an improved tracking method is provided that fully utilizes the fine temporal resolution of the list-mode format. Similar to PEPT, the method according to the current invention performs trajectory reconstruction directly from raw list-mode measurements. Rather than an image, our method uses a B-spline to model the trajectory of a single source. This model is advantageous because it incorporates the continuous nature of spatiotemporal motion, which allowed us to achieve higher tracking accuracy.

One of the main finding of this experiment is that within a "feasible range", tracking accuracy (as defined in Eq. 6) depends primarily on a single parameter, the average number of counts per spline interval. As long as this ratio remains constant, tracking accuracy is independent of activity and velocity. In this exemplary experiment, most of the reconstructions were performed using 5 counts per spline interval, but larger spline intervals can be used as well (FIG. 7).

It was also found that tracking accuracy is not simply equal to the spatial resolution of the PET system used for tracking (FIG. 8). For small-animal PET imaging, spatial resolution is primarily determined by the size and configuration of the detectors. Other factors such as acolinearity and positron range are negligible due to the small bore of small-animal imaging systems and the short range of $^{18}F$ positrons. Perhaps counter-intuitively, a given PET system can track a point source with far better accuracy than its spatial resolution would suggest. This is because the position of a source, when estimated from many independent measurements, can be known with a variance inversely proportional to the number of measurements, as clearly shown by FIG. 7. Conceptually, the 3D position of a static point source can also be estimated from a tomographic PET image with accuracy better than the spatial resolution of PET—for instance, by computing the center of mass of the image.

The performance of a tracking algorithm is also defined by its ability to track a fast-moving source using as few counts as possible. Empirically, we found that the feasibility of source tracking is determined by a linear relationship between the activity and velocity of the source (FIG. 6C). This relationship can be generalized to yield the range F of point sources that can be tracked:

$$F=\{(a,v): v < \varepsilon \cdot s \cdot a\}, \quad (7)$$

where a is the source activity, v the source velocity, s the sensitivity of the PET system, and ε a parameter. The parameter ε has units of distance and can be physically interpreted as the average distance traveled by the point source between two detected counts. Thus, a tracking algorithm that achieves a higher ε requires fewer counts to successfully track a moving source. This parameter is called the tracking efficiency. This metric is largely independent of the scanner characteristics and depends only on the reconstruction parameters, that is, the number of counts per spline interval.

It follows from this discussion that the performance of a tracking algorithm can be fully characterized by two global metrics, the tracking accuracy and the tracking efficiency. The two metrics relate however to competing objectives, which can be balanced by adjusting the length of the spline intervals. Longer spline intervals increase tracking accuracy but hinder tracking efficiency. To better understand how these two metrics relate to each other, we reran the analysis of FIG. 6C using different spline parameters, ranging from 5 to 100 counts per spline intervals. It was then computed tracking accuracy and efficiency for each spline parameterization. The results of this analysis, which are summarized in FIG. 10, show that tracking efficiency and accuracy are linearly related. An increase in tracking efficiency (beneficial) implies a linear increase in tracking accuracy (detrimental).

The concept of tracking accuracy and tracking efficiency can be applied to estimate how the tracking method used in PEPT would compare to spline tracking. PEPT can track a point source moving 2 m/s with accuracy as low as 0.5 mm, using 105 counts/s. Based on these numbers, the tracking efficiency of PEPT is approximately 0.02 mm. As shown on FIG. 10, the spline tracking method can achieve similar accuracy but 20-fold better efficiency, meaning that a fast-moving source can be tracked using 20 times fewer counts.

This finding is significant, given that radiolabeling efficiency is the limiting factor for tracking single cells. The better tracking efficiency is achieved by representing the motion of the source using a smooth spline function rather than a discrete number of static positions. On the other hand, it should also be mentioned that PEPT acquisitions tend to suffer from a higher rate of scatter and randoms, which could also be a factor contributing to the lower tracking efficiency.

Having established the requirements for tracking a single point source in silico, a comment is provided herein on how this method translates into the real world. As shown in FIGS. 9A-9B, at high activity levels, the experimental findings are fully consistent with the simulation results. However, at low activity levels, a discrepancy arises due to the fact that our computer simulations do not account for the natural radio-activity of $^{176}Lu$, which is present in LSO detectors (natural abundance, 2.6%). This isotope decays with a half-life of $3.8 \times 10^{10}$ years by emitting a beta particle (endpoint energy of 596 keV) and a cascade of prompt gamma photons (primarily 202 and 307 keV). This intrinsic radioactivity yields a background coincidence rate that may overshadow the weak signal from a single radiolabeled cell. A study of the Inveon found that the count rate from intrinsic $^{176}Lu$ decay was equivalent to a 100 Bq source (lower-level discriminator of 400 keV). Therefore, it is conjectured that single-cell tracking will ultimately be limited to PET systems built from non-lutecium scintillator materials, such as bismuth germinate (BGO) or lanthanum bromide (LaBr3). As found in a recent comparison study, the background rate in a clinical BGO PET scanner is 1000 times lower than in an equivalent LSO scanner. This suggests that <1 Bq equivalent background rate could be achieved for a small-animal scanner equipped with BGO detectors.

Reconstructing the trajectory of a single cell may also have clinical applications. A growing number of clinical studies are using PET imaging to track cells during cell-based therapies. The ability to track and reconstruct the trajectory of single cells may reveal new dynamic behaviors of cells following their transplantation in vivo. From a conceptual standpoint, the trajectory reconstruction algorithm of the current invention could be applied to whole-body clinical PET scanners. However, the configuration of these scanners is less amenable to single-cell tracking Clinical PET scanners have lower sensitivity and higher scatter fraction than preclinical systems. This may hinder the precise localization of a weakly emitting cell. Furthermore, a clinical scanner has limited axial coverage and cannot follow the circulation of a cell at the whole-body level. Despite these drawbacks, tracking single sources may be possible with clinical scanners but it will likely require labeling the cells with higher activity. Time-off light information could also be used within this framework to increase the accuracy of the localization.

Using computer simulations, the performance of a novel algorithm designed to estimate the spatiotemporal trajectory of a moving source directly from list-mode PET data was demonstrated. The invention was also successfully tested using experimentally acquired PET data. This invention models the trajectory of the source as a 3D spline of the temporal variable and does not require tomographic images to be reconstructed in the conventional sense. A key aspect of the current invention can be summarized by the following equation, which relates the best achievable tracking accuracy to the activity and velocity of the source, and to the sensitivity of the PET system:

$$T \approx 0.3 \text{ mm} + 0.5 \cdot \frac{v}{s \cdot a} \qquad (8)$$

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example the trajectory reconstruction algorithm may be a useful tool for estimating breathing motion during 4D PET/CT imaging. This approach could provide a data-driven method for gating the reconstruction of the emission images. Another application where tracking may be useful is in emission-guided radiation therapy, a recently proposed technique in which radiotracer uptake is used to estimate tumor position in real time during delivery of radiation therapy. Other variations include tracking multiple moving sources simultaneously.

All such variations are considered to be within the scope and spirit of the present invention as defined by the following claims and their legal equivalents.

What is claimed:

1. A method of reconstructing time-varying positions of an individual radioactive cell, comprising:
   a. transplanting to a human or animal host a radioactive cell;
   b. acquiring a positron emission tomography (PET) scan, using a PET scanner, of said human or said animal host to obtain a list of coincidence events containing lines and corresponding timestamps;
   c. using a computer to:
      i. model a time-varying position of said radioactive cell as a 3D function of a temporal variable;
      ii. determining an average distance for different parameters of said 3D function, wherein said average distance is determined by computing a geometrical distance between one said line in said list of coincidence events and a 3D position given by said 3D function for said timestamp corresponding to said one line, wherein an average of all said computed geometrical distances is computed;
      iii. iteratively repeating said modeling step i) and said average distance determination of step ii) until said average distance converges to a minimum distance; and
   d. reconstructing a time-varying position of said radioactive transplanted cell, using said PET scanner, by outputting said 3D function of said temporal variable of said reconstructed time-varying position of said transplanted radioactive cell, wherein said reconstructed time-varying position provides an estimate of individual cell migration in real time inside said human or animal host.

2. The method of claim 1, wherein said 3D function comprises a B-spline function of said temporal variable.

3. The method according to claim 1, wherein a regularization term is added to said geometrical distance to favor desirable trajectories over undesirable trajectories, wherein if no said list of coincidence events are detected over a pre-defined time interval, a shortest trajectory is selected from available said list of coincidence events.

4. The method of claim 1, wherein said geometrical distance comprises a mean-square distance.

5. The method according to claim 1, wherein said computing a geometrical distance comprises assigning a constant value to events that have a geometrical distance greater than a predefined distance $d_{max}$.

* * * * *